(12) United States Patent
Nomura et al.

(10) Patent No.: US 7,732,015 B2
(45) Date of Patent: Jun. 8, 2010

(54) PROCESS FOR PRODUCING NANOPARTICLE OR NANOSTRUCTURE WITH USE OF NANOPOROUS MATERIAL

(75) Inventors: Shintaro Nomura, Tsukuba (JP); Hironori Itoh, Tsukuba (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 535 days.

(21) Appl. No.: 11/597,877

(22) PCT Filed: May 31, 2005

(86) PCT No.: PCT/JP2005/009990
§ 371 (c)(1), (2), (4) Date: Nov. 29, 2006

(87) PCT Pub. No.: WO2005/115609
PCT Pub. Date: Aug. 12, 2005

(65) Prior Publication Data
US 2008/0085364 A1   Apr. 10, 2008

(30) Foreign Application Priority Data
May 31, 2004   (JP) .............................. 2004-162650

(51) Int. Cl.
*B05D 3/12* (2006.01)
(52) U.S. Cl. .................. 427/277; 427/355; 427/256; 427/271; 427/369
(58) Field of Classification Search ................. None
See application file for complete search history.

(56) References Cited

U.S. PATENT DOCUMENTS
6,359,288 B1 * 3/2002 Ying et al. .................... 257/14
(Continued)

FOREIGN PATENT DOCUMENTS
JP   05220966 A * 8/1993
(Continued)

OTHER PUBLICATIONS
Fabrication of Nanoring Arrays by Sputter Redeposition Using Porous Alumina Templates, Hobbs et al, Published Nov. 26, 2003, Nano Letters 2004 vol. 4, No. 1, p. 167-171.*
(Continued)

*Primary Examiner*—Michael Cleveland
*Assistant Examiner*—Alex Rolland
(74) *Attorney, Agent, or Firm*—Westerman, Hattori, Daniels & Adrian, LLP

(57) ABSTRACT

A nanostructure including a nanoporous material having micropores filled with a fragmented thin-film material from the opening-side of each micropore, the nanoporous material being obtained by placing a thin-film material on a surface of a nanoporous material and pressing the thin-film material so that the thin-film material is cut out at the surface edge of each micropore of the nanoporous material and pressed into the micropore. By removing the nanoporous material form the nanoporous material, microparticles constituted from the thin-film material that filled the nanoporous material are obtained. By covering all the wall surfaces of the micropores of the nanoporous material in advance, nanocapsules each constituted from a tubular structure composed of the thin film covering the entire wall surface of the micropore and a cover made of a thin-film material filled in the vicinity of the opening of the micropore can be formed.

7 Claims, 8 Drawing Sheets

U.S. PATENT DOCUMENTS

| | | | |
|---|---|---|---|
| 6,946,597 B2 * | 9/2005 | Sager et al. | 136/263 |
| 7,435,488 B2 * | 10/2008 | Tomita et al. | 428/702 |
| 2003/0020060 A1 * | 1/2003 | Iwasaki et al. | 257/13 |

FOREIGN PATENT DOCUMENTS

| | | |
|---|---|---|
| JP | 6-32675 A | 2/1994 |
| JP | 11-200090 A | 7/1999 |
| JP | 2000-285791 A | 10/2000 |
| JP | 2001-139317 A | 5/2001 |
| JP | 2001-166717 A | 6/2001 |
| JP | 2002-277659 A | 9/2002 |
| JP | 2003-73859 A | 3/2003 |
| JP | 2003-128832 A | 5/2003 |
| JP | 2004-130171 A | 4/2004 |
| JP | 2004-330330 A | 11/2004 |
| JP | 2005-95733 A | 4/2005 |

OTHER PUBLICATIONS

R. C. Furneaux et al.; "The formation of controlled-porosity membranes from anodically oxidized aluminium", Nature, vol. 337, Jan. 12, 1989, pp. 147-149.

H. Masuda et al.; "Fabrication of Gold Nanodot Array Using Anodic Porous Alumina as an Evaporation Mask", Japan J. Appl. Phys. vol. 35, Part.2, No. 1B, Jan. 15, 1996. pp. L126-L129.

"High Ordered Metal Nano-Hole Array Using Anodized Alumina", vol. 31, No. 5, 1996.

International Search Report of PCT/JP2005/009990, date of mailing: Jul. 26, 2005.

* cited by examiner

2 Porous Alumina Layer
1 Aluminum Substrate

3 Dent
1A

7 Thin Film
2A
1A

5 Pressing Member
7 Thin Film
7A
6
2A
1A

250nm
Thickness of Deposited Gold 10nm

250nm
Thickness of Deposited Gold 20nm

250nm
Thickness of Deposited Gold 30nm

500nm

PROCESS FOR PRODUCING NANOPARTICLE OR NANOSTRUCTURE WITH USE OF NANOPOROUS MATERIAL

TECHNICAL FIELD

The present invention relates to processes for producing microparticles and nanostructures from thin-film materials by using nanoporous materials.

BACKGROUND ART

Microparticles are usually defined as particles 1 nm to 1 μm in size. Microparticles by themselves are used as stable monochromatic fluorescent particles or magnetic particles; in addition, they are used as building blocks of tunable light-emitting diodes, single-particle transistors, very-high-density magnetic recording media, and the like. In recent years, their fields of application have expanded along with technological advancement in individual fields, and this has led to an increase in demand.

There have been many reports on such microparticles including a metal, such as gold, platinum, or nickel, or a compound such as titanium oxide, zinc oxide, cadmium selenide, and zinc sulfide. As the production process therefor, a homogeneous precipitation method, a hydrothermal synthesis method, a hot-soap method, and the like have been known.

It has also been known that a porous oxide film having nanoholes periodically arranged into a triangular array at nanoscale intervals can be formed by an anodization process of aluminum (for example, nonpatent document 1). By carrying out a two-step anodization process, a periodic structure of nanoholes with improved regularity, perpendicularity, linearity, and independence can be formed (nonpatent document 2).

By using a method of filling nanoholes in an anodized film with a metal, semiconductor, or the like or a nanohole replica method, various applications have been attempted including coloring, magnetic recording media, EL light-emitting elements, electrochromic elements, optical elements, solar cells, gas sensors, and the like (patent documents 1 to 9). Furthermore, nanoholes are expected to be applied to various other fields including quantum devices such as quantum wires and MIM elements and molecular sensors with nanoholes used as chemical reaction sites (nonpatent document 3).

Nonpatent document 1: R. C. Furneaux, W. R. Rigby & A. P. Davids "NATURE" Vol. 337, p. 147 (1989)
Nonpatent document 2: Jpn. Journal of Applied Physics, Vol. 35, Part 2, No. 1B, pp., L 126-L 129, 15 January (1996)
Nonpatent document 3: Masuda "Kotai Butsuri [Solid Physics]" 31, 493 (1996)
Patent document 1: Japanese Unexamined Patent Application Publication No. 06-32675 (Patent No. 3004127)
Patent document 2: Japanese Unexamined Patent Application Publication No. 11-200090
Patent document 3: Japanese Unexamined Patent Application Publication No. 2000-285791
Patent document 4: Japanese Unexamined Patent Application Publication No. 2001-139317
Patent document 5: Japanese Unexamined Patent Application Publication No. 2001-166717
Patent document 6: Japanese Unexamined Patent Application Publication No. 2002-277659
Patent document 7: Japanese Unexamined Patent Application Publication No. 2003-073859
Patent document 8: Japanese Unexamined Patent Application Publication No. 2003-128832
Patent document 9: Japanese Unexamined Patent Application Publication No. 2004-130171

DISCLOSURE OF INVENTION

Problems to be Solved by the Invention

According to the processes of producing microparticles of the related art described above, it has been difficult to produce large amounts of nano-size microparticles with uniform size at low cost. Moreover, the types of raw materials usable in the production are limited. Furthermore, although a technology of using a nanoporous material, such as anodized film, in which micropores with several tens nanometers in diameter are two-dimensionally arrayed is under development, it has been difficult to produce electronic devices, optical devices, and magnetic devices in which microparticles are independently arrayed in a desired pattern over a wide range. Although a technology of filling the pores with a metal from the bottom of the pores by an electrodeposition method or a sol-gel method has been known, a process of covering the opening of each micropore or a process of producing nanocapsules have not been available.

Means for Solving the Problems

The present invention provides a process that can fill open pores of a nanoporous material with a desired material from their openings and a process that can cover the individual pores of the nanoporous material with a desired material under various conditions including in air, in liquid, in vacuum, at high temperature, and at low temperature. Moreover, it provides microparticles and devices such as nanocapsules produced by a process that includes the above-described process as one of the steps.

In particular the present invention provides: (1) a process for producing a nanostructure, including: disposing a thin-film material on a surface of a nanoporous material; pressing the thin-film material with a pressing member so that the thin-film material is cut out by surface edges of micropores of the nanoporous material and pressed into the interior of each micropore, wherein a nanostructure including a nanoporous material in which the thin-film material is separated and filled in the interior of each micropore from an opening of the micropore is formed thereby.

The present invention also provides: (2) the process of producing the nanostructure according (1) above, in which the thin-film material is placed on the surface of the nanoporous material in portions other than the openings of the micropores so that the thin-film material can be separated and filled by forming a nanoring shape.

The present invention also provides: (3) the process of producing the nanostructure according to (1) above, in which the pressing member is a spatula or a ball.

The present invention also provides: (4) a process of producing microparticles, including removing the nanoporous material from the nanoporous material in which the thin-film material is separated and filled in the interior of each micropore according to any one of (1) to (3) above, wherein the thin-film material that filled the micropores obtained thereby form the microparticles.

The present invention also provides: (5) a process of producing nanocapsules, including: coating all pore wall surfaces of a nanoporous material with a thin film; placing a thin-film material on a surface of the nanoporous material; pressing the thin-film material so that the thin-film material is cut out by surface edges of micropores of the nanoporous material and pressed into the interior of each micropore, thereby forming a nanoporous material in which the thin-film material is separated and filled only in the vicinity of an opening of each micropore; and removing the nanoporous material to thereby form a nanocapsule constituted from a tubular structure formed from the thin film that coats the entire wall surface of each micropore and a cover composed of the thin-film material filled in the vicinity of the opening of the micropore.

The process of producing microparticles according to the present invention involves placing a thin film on a surface of a nanoporous material by any means including vapor deposition, scooping the thin film in a liquid, simply placing the film, or the like, and then pressing the thin film so that the thin film is mechanically pressed into the nanoporous material. Here, by appropriately choosing (1) the hardness of the nanoporous material, (2) the hardness of the thin-film material to be pressed, and (3) the pressure during the pressing, the nanoporous material and the thin-film material to be pressed are appropriately deformed, and a slightly irregular surface of the nanoporous material tightly adheres to the surface of the pressing member over a wide region. In addition, (4) by adequately selecting the hardness and viscosity of the thin-film material, the pressed thin-film material tears and separates from the film by being pressed into the micropores. Accordingly, (5) by adequately choosing the frictional force between the thin film material and the pressing member, the separated microparticles remain inside the micropores without adhering to the pressing member.

According to the process of the present invention, the thin-film material are divided into fine fragments having substantially the same size as the micropore diameter of the nanoporous material, and these separated fragments of the thin film material form independent microparticles regularly arranged in micropores of the nanoporous material one-by-one. In this process, nanoring-shaped microparticles can be formed by placing the thin-film material on a surface in portions other than the openings of the micropores of the nanoporous material. The inner diameter of the nanorings can be controlled by adjusting the amount of the thin-film material. Moreover, by selectively removing the nanoporous material by etching or the like, microparticles can be recovered from the nanoporous material. According to this process, uniformly sized nanosized microparticles can be produced in large numbers in a shorter time. Furthermore, by pressing the thin-film material into only the vicinity of the opening of each micropore of the nanoporous material, the micropore can be covered with the thin-film material. The micropores formed in the vicinity of the opening of each micropore of the nanoporous material can be heated to impart roundness to the shape or to widen the intervals between the microparticles to clarify the boundaries and avoid contact.

After a thin-film composed of a material that forms a capsule is provided to cover the wall surfaces of the micropores of the nanoporous material, covers may be formed with the thin-film material and then the nanoporous material may be removed by etching or the like to integrally form capsules each constituted from a tubular structure and a cover. Before providing the cover, a substance to be contained in the capsule is introduced into the micropores. In this manner, various chemicals and liquids can be sealed inside by forming covers composed of a thin-film material after the chemicals and liquids are introduced inside the nanoporous material.

According to this process, microparticles and covers that directly have physical properties of the thin-film material can be produced as long as the thin-film material can be formed on the surface of the nanoporous material. Thus, the variety of the microparticles to be produced and the variety of the materials for the cover can be widened. Moreover, the process can be implemented under various conditions including in air, in liquid, in vacuum, at high temperature, and at low temperature.

Effects

According to the process of the present invention, uniformly sized and nanosized microparticles can be produced at a shorter time in large numbers using low-cost equipment, and the variety of the materials usable for the microparticles is wide. According to the process of the present invention, electronic devices, optical devices, magnetic devices, synthetic lattice quantum dots, and the like in which these microparticles are independently arrayed into a desired pattern over a wide area can be provided. A process of forming nanocapsules is also provided.

BEST MODE FOR CARRYING OUT THE INVENTION

A process of the present invention involves placing a thin film on a surface of a nanoporous material by any means including vapor deposition, scooping the thin film in a liquid, simply placing the film, or the like, and then pressing the thin film so that the thin film is cut out at the edge of each micropore and the cutout portion is pressed into the micropore. In this manner, independent microparticles composed of a thin-film material can be arrayed into a pattern of micropores.

The thin-film material is preferably softer than the nanoporous material and a pressing member and causes less friction with the pressing member. The thickness of the thin-film material is preferably 1 to 100 nm. The thin-film material may be any one of metal, inorganic substances, and organic substances and may be any one of a self-supporting film, such as a metal thin film, a thin film formed on a surface of the nanoporous material by vapor deposition, plating, or the like, and a thin film made by applying and solidifying a paste material.

The material for the pressing member is preferably a material harder than the coating material but soft enough to appropriately deform and adhere to the surface of the nanoporous material when pressed. In order to allow microparticles formed inside the micropores as a result of the pressing to remain inside the micropores, the material preferably causes low friction with the thin-film material. Therefore, a plastic or metal spatula with a smooth curved surface is preferable; however, the pressing member is not limited to spatulas.

For example, a ball composed of a material having an appropriate hardness, such as a plastic or metal ball, may be used so that the ball presses the surface of the nanoporous material as it rolls. The size of ball is preferably about 0.1 mm to 2.0 mm. The ball presses the nanoporous material as it rolls. When a ball is used as the pressing member during pressing, adhesion to the surface of the nanoporous material is improved, and uniformity in size and shape of nanoparticles produced is thereby improved. Since the ball presses the surface of the nanoporous material as it rolls, it becomes possible to prevent deformation and damage of the nanoporous material or the pressing member. Furthermore, since adjacent microparticles are prevented from coming into contact with each other by applying a higher pressure, independence of individual microparticles is improved, and the range of usable materials is expanded.

It is required for the thin-film material to tear and be pressed into micropores. In order to do this, the thin-film material to be pressed must be slipped on the surface of the nanoporous material. For example, by allowing a spatula to slide to press the surface of the nanoporous material via the thin-film material, the thin-film material can be filled from the openings of the nanoporous material or can be used to cover the micropores of the nanoporous material.

Various microparticle array patterns and thin-film-forming regions are conceivable from the combination of the micropore pattern of the nanoporous material and the thin-film-forming region.

After the thin-film material is filled, the nanoporous material is removed by etching or the like to obtain microparticles composed of the infilling thin-film material. Furthermore, after the thin-film material is filled, a substrate material may be placed on the surface of the nanoporous material by any means such as vapor deposition, application, or the like, and the nanoporous material may be selectively removed by etching or the like to produce a device in which microparticles arrayed in a micropore pattern are transferred to the substrate material.

Gold microparticles arrayed on a substrate by the process of the present invention have their polariton dispersion controlled by the arraying. Therefore, they can be used as narrow-band light-absorbing/reflecting devices and optical switching devices based on polariton resonance. Furthermore, for example, by producing microparticles by using a semiconductor thin film such as indium antimony, an electronic device and a magnetic device in which the ferromagnetic-paramagnetic phase transfer can be controlled by interparticle bonds.

A nanoporous material formed naturally, such as zeolite, or a nanoporous material produced by any of various methods such as an anodization method, a nano-indent method, and a lithographic method, can be used as the nanoporous material used in the present invention. However, by using an anodization method of aluminum, the production can be facilitated and the production cost can be reduced. An alumina nanoporous material prepared by an anodization method has the advantages such as that nanoholes are arranged in a triangular array over a large area, that a large numbers of micropores can be formed at the same time by self-assembly, that the size of the micropores is uniform, that the micropore diameter is controlled to 20 nm to 500 nm, etc.

First Embodiment

A process of producing microparticles according to the process of the present invention will now be described. As schematically shown in FIG. 1, an aluminum substrate 1 planarized by electropolishing or the like is anodized to form an anodized porous alumina layer 2 thereon. Subsequently, only the anodized porous alumina layer 2 is removed by etching or the like to prepare an aluminum substrate 1A having dents 3 arranged into a triangular array, the aluminum substrate 1A having a cross-section schematically shown in FIG. 2.

It is known that in order to form dents arranged into a triangular array, special anodization conditions must be satisfied. For example, dents arranged into a triangular array are produced by anodizing a sample for 12 hours at 40 V in 0.3 M oxalic acid as an electrolyte at 0° C. and then immersing the sample in a phosphoric acid (6 wt %)/chromic acid (1.8 wt %) mixed solution at 60° C. for 60 minutes to remove the alumina layer.

A thin film 4 is formed on a surface of the aluminum substrate 1A. As shown in the cross-sectional view of FIG. 3, a pressing member 5 having a round tip is gently slid in one direction while being pressed onto the aluminum substrate 1A with the thin film 4 therebetween. In this manner, the thin film 4 is cutout at the edges of the dents 3 arranged into a triangle array, thereby forming microparticles 4A. Although the microparticles are fixed on the surface of the aluminum substrate, they can be separately recovered as uniformly sized microparticles having a shape transferred from the shape of the dents by removing the aluminum substrate by etching or the like. In order to slide the spatula by a mechanical method, a supporting shaft of the spatula may be fixed to a miller to apply a predetermined pressure and the substrate may be moved by using an XYZ stage to uniformly apply pressure.

Second Embodiment

A process of filling a thin-film material from the openings of the nanoporous material and a process of covering the micropores of the nanoporous material with the thin-film material according to the present invention will now be described. An aluminum substrate which has a cross-section schematically shown in FIG. 2 and which has dents arranged in a triangle array is anodized, and, as shown in the schematic view of FIG. 4, an anodized porous alumina layer 2A having a periodic structure of micropores 6 with improved regularity, perpendicularity, linearity, and independence is formed.

Next, as schematically shown in FIG. 5, a thin film 7 is disposed on a surface of the anodized porous alumina layer 2A. Next, as shown in a schematic cross-sectional view in FIG. 6, a pressing member 5 having a round tip is gently slid in one direction while pressing the substrate with the thin film 7 therebetween. In this manner, the thin film 7 is cut out at the edges of the micropores such that microparticles 7A of the thin-film material are filled only in the vicinity of the opening of each micropore 6 of the porous alumina layer 2A. By this process, it becomes possible to allow filling of the thin-film material from the openings of the micropores of the nanoporous material or to cover the vicinity of the opening of each micropore of the nanoporous material with the thin-film material. Furthermore, the microparticles 7A can be heated to impart roundness to their shape or to widen the space between microparticles so as to clarify the boundaries and prevent contact.

Third Embodiment

A process of producing microparticles according to the present invention will now be described. When the thin-film material is to be filled in only the vicinity of the surface of the micropores in the second embodiment, it is sometimes difficult to press the entire surface of the porous alumina layer having a large area, e.g., 250 mm² as shown in the first embodiment, with a pressing member without allowing any clearance. In such cases, a non-pressed portion of the thin-film material may remain on the surface of the porous alumna layer. The non-pressed portion of the thin-film material becomes wasted in the later stage of recovering microparticles from the porous alumina layer. However, when the thin-film material is a conductor and the non-pressed thin-film material is brought into contact with an anode to conduct anodization for few seconds under the same conditions as making the porous alumina layer, the porous alumina layer underneath the non-pressed portion of the thin film slightly melts, and bubbles generated at the electrode during the anodization attach to the thin-film material. As a result, only non-pressed portion of the thin film is separated and removed from the surface of the nanoporous material, and only the independent microparticles remain on the surface of the porous material.

The microparticles are fixed to interiors of the micropores of the porous alumina layer. However, by etching away the porous alumina layer with a phosphoric acid (6 wt %)/chromic acid (1.8 wt %) mixed solution or a 1.0 wt % sodium hydroxide aqueous solution, uniformly sized microparticles having a shape transferred from the shape of the porous alumina micropores can be separately recovered.

Fourth Embodiment

A process of producing nanoring-shaped microparticles according to the present invention will now be described. A thin film 4 is placed on a surface of an anodized porous alumina layer 2A schematically illustrated in FIG. 7 in the portions other than the openings of micropores 6. A dipping method in an application solution, vapor deposition, or the like may be employed to place the thin film 4. Subsequently, a pressing member 5 having a round tip is gently slid in one direction while pressing the substrate with the thin film 4 therebetween. The material of the thin film 4 is deposited on the rim of the opening of each micropore as a result of pressing, and nanorings 12 are thereby formed.

The inner diameter of the nanorings 12 can be controlled by the amount of the thin film 4 placed on the anodized porous alumina layer 2A. When the amount of the thin film 4 is small, the inner diameter of the nanorings 12 is increased. The inner diameter of the nanorings 12 decreases as the amount of the thin-film 4 is increased. If the amount of the thin film 4 is sufficiently large, the nanorings 12 become completely closed, thereby forming microparticles. With the same amount of the material, the inner diameter increases as the outer diameter of the micropores increases.

The outer diameter of the nanorings 12 is determined based on the size of the micropores 6 of the anodized porous alumina layer 2A. The outer diameter of the nanorings 12 is typically 30 nm to 500 nm. When the nanorings are formed using a superconducting material, they can be used as memory devices or switching devices since a magnetic flux can be individually confined in the periodically arrayed nanorings. Moreover, nanorings made of a magnetic material can be used in magnetic recording device applications. Furthermore, by irradiating non-magnetic metal nanorings with light, a specific electric field is formed inside each ring, and a large nonlinear optical effect is considered to occur by the combination with a nonlinear optical material. Accordingly, the nanorings can be used in optical device applications.

Fifth Embodiment

A process of producing nanocapsules according to the present invention will now be described. A thin film 8 for forming tubular structures for capsules are formed over all the wall surfaces of micropores 6 of an anodized porous alumina layer 2A schematically shown in FIG. 4 to form a cross-sectional structure schematically shown in FIG. 8. Dipping in a coating solution, vapor deposition, or the like can be employed to coat all the wall surfaces of the micropores 6 with the thin film for forming tubular structures. For, example, the micropores of the anodized porous alumina layer 2A may be filled with a resin material such as poly (methyl methacrylate) (PMMA) dissolved in a solvent. After filling, the solvent is dried in air at room temperature. The volume of the resin is decreased as a result of evaporation of the solvent, and the resin adheres to the micropore wall surfaces because of the surface tension, thereby forming tubular structures. Next, a thin film 9 for covering composed of the same thin-film material as that of the thin film 8 for forming tubular structures of capsules is placed on the surface of the anodized porous alumina layer 2A.

Subsequently, as show in a schematic cross-sectional view in FIG. 9, a pressing member 5 with a round tip is gently slid in one direction while pressing the substrate via the thin film 9. In this manner, the thin film 9 is cut out by the surface edges of the micropores, and only the vicinity of the opening of each micropore 6 of the anodized porous alumina layer 2A is filled with a microparticle 9A of the thin-film material. As a result, each micropore is independently sealed with the cover 9A of the same material as that of the capsule coating material, thereby forming a nanocapsule. A variety of materials can be charged in the nanocapsule by allowing environment E around the anodized porous alumina layer to contain a capsule filler material 10. The filler material can be introduced as long as it is a particle, molecule, liquid, or gas smaller than the capsule. Examples thereof include anticancer agents, pigments for use as markers, and chlorine gas.

By removing the anodized porous alumina layer 2A through selective etching, nanocapsules 11 each of which is constituted from a tubular structure composed of the capsule thin-film material 8 and a cover attached to the upper rim of the interior of the tubular structure through intermolecular force and containing the capsule filler material 10 can be separately recovered.

EXAMPLE 1

Gold microparticles were produced by the process of the present invention. A pure aluminum (99.999%) substrate (25 mm in length, 10 mm in width, and 0.5 mm in thickness) was anodized in a 0.3 M oxalic acid solution at 0° C. and 40 V for 12 hours to make an anodized porous alumina layer. Subsequently, only the anodized porous alumina layer was removed using a phosphoric acid (6 wt %)/chromic acid (1.8 wt %) mixed solution. As a result, an aluminum substrate having dents arranged in a triangle array was obtained. The rims of the dents were edged. The center-to-center distance d between adjacent dents was about 100 nm (100 nm interval). The depth of the dent was about 10 nm.

Gold was deposited on a surface of the aluminum substrate to a thickness of 50 Å. A polystyrene spatula with a round tip having a radius of curvature of about 0.5 mm as a pressing member was gently slid by hand once in one direction while pressing the aluminum substrate via the gold thin film. As a result, the gold thin film was pressed into the dents arranged in a triangle array.

FIG. 11 is a SEM photograph of the surface. As shown in FIG. 11, the gold thin film was cut at edges of the dents, and about 100,000,000 uniformly sized gold microparticles having a diameter corresponding to the diameter (about 100 nm) of the dents were formed in the pressed region of about 1 mm$^2$ on the surface of the aluminum substrate. The aluminum substrate was removed by dissolving with a 1.0 wt % aqueous sodium hydroxide solution to separately recover the gold microparticles having a shape transferred from the dents.

EXAMPLE 2

Micropores of a nanoporous material were covered with a thin-film material according to the process of the present invention. An aluminum substrate having dents arranged in a triangle array was prepared as in EXAMPLE 1. The aluminum substrate was anodized for 20 minutes at 0° C. and 40 V in a 0.3 M oxalic acid solution to form an anodized porous alumina layer. The surface of the porous alumina layer locally showed extremely high flatness; however, in a large region of several tens micrometers or more, slight irregularities of about 1 μm resulting from electropolishing were observed.

Subsequently, a gold thin film having a thickness of 100 Å was allowed to float on water surface and scooped with the aluminum substrate to place the gold thin film on the surface of the anodized porous alumina layer. A polystyrene spatula with a round tip having a radius of curvature of about 0.5 mm was then gently slid by hand once in one direction while pressing the aluminum substrate via the gold thin film. As a result, the gold thin film was cut out at the surface edges of the micropores and pressed into vicinity of the opening of each micropore. A SEM photograph of the surface is shown in FIG. 12. As shown in FIG. 12, microparticles of the gold thin film filled the vicinity of the opening of each micropore in the porous alumina layer.

EXAMPLE 3

Gold microparticles were prepared under the same conditions as in EXAMPLE 1 except that gold was deposited to a thickness of 50 nm and a stainless steel ball having a diameter of 0.5 mm was used as a pressing member by rolling the ball with hand. FIG. 13 is a SEM photograph of the surface. As shown in FIG. 13, an array of uniformly sized and uniformly shaped gold nanoparticles was obtained throughout a length of several centimeters with a width of about 0.2 mm by pressing the gold film into the micropores of the nanoporous material having micropores arranged in a 100 nm interval. This gold nanoparticle array was annealed for 5 minutes at 600° C. in a nitrogen atmosphere. As a result, as shown in FIG. 14, the shape became round, the space between microparticles was widened, and the boundaries were clarified.

EXAMPLE 4

Gold microparticles were formed inside micropores arrayed at an interval of 100 nm in the nanoporous material under the same conditions as in EXAMPLE 3 except that gold was deposited to a thickness of (a) 10 nm, (b) 20 nm, and (c) 30 nm. FIGS. 15(a), (b), and (c) are SEM photographs of the respective surfaces. Nanorings with an outer diameter of about 90 nm and an inner diameter of about 40 nm were formed when the thickness of gold was 10 nm, and nanorings with an outer diameter of about 90 nm and an inner diameter of about 20 nm were formed when the thickness of gold was 20 nm. When the thickness of gold was 30 nm, rings were completely closed, and disk-shaped nanoparticles having an outer diameter of about 90 nm were formed.

EXAMPLE 5

Gold nanoparticles were formed under the same conditions as EXAMPLE 4 except that gold was deposited on a nanoporous material having micropores arranged at a 400 nm interval, to a thickness of 50 nm. FIG. 16 is a SEM photograph of the surface. As shown in FIG. 16, nanorings with an outer diameter of about 390 nm and an inner diameter of about 250 nm were formed.

EXAMPLE 6

Nanocapsules were formed by the process of the present invention. A thin film for capsule tubular structures was applied in vacuum on a surface of an anodized porous alumina layer having micropores with a depth of 300 nm and a diameter of 100 nm formed by the same method as in EXAMPLE 2. As the material of the thin film, poly(methyl methacrylate) (PMMA) in a 1-acetoxy-2-ethoxyethane solvent was used. As a result, micropores were completely filled with PMMA. By drying the solvent in air at room temperature, the volume of PMMA decreased. Because the volume of PMMA decreased while PMMA was adhering to the micropore wall surface by the surface tension, the PMMA was formed into tubular structures. Next, in air at 1 atm, PMMA was applied on the surface of the porous alumina layer by spin coating to a thickness of 50 nm, and PMMA separately filled each of the micropores of the porous alumina layer by the same method as in EXAMPLE 2.

Subsequently, the anodized porous alumina layer was removed by dissolving with an aqueous sodium hydroxide solution. Nanocapsules were separately recovered.

INDUSTRIAL APPLICABILITY

The present invention provides a novel process for producing nanosized independent microparticles with uniform size and thereby can provide nanosized microparticles of various materials at low cost. The present invention can also provide electronic devices, optical devices, magnetic devices, synthetic lattice quantum dots, and the like in which these microparticles are independently arrayed into a desired pattern. The present invention can further provide a process of producing nanocapsules in which a variety of chemicals and liquids are filled in a nanoporous material.

Figure 1:
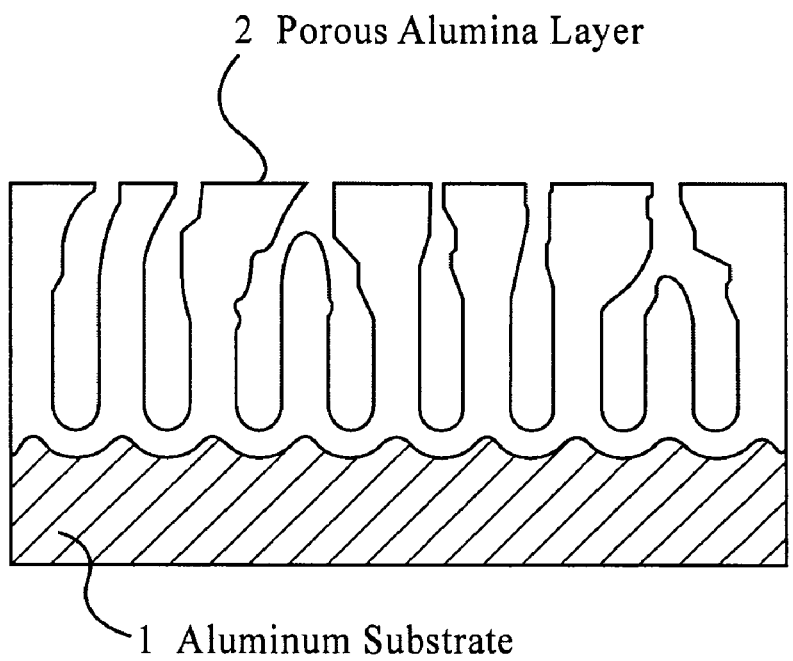
FIG. 1 is a schematic cross-sectional view of an anodized porous alumina layer formed in a first embodiment.
Figure 2:
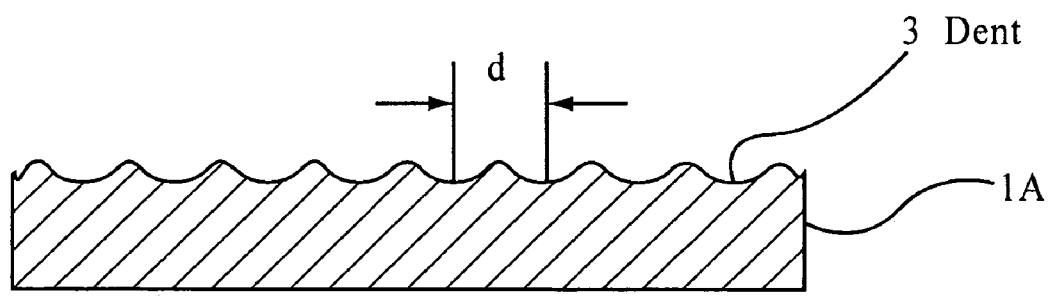
FIG. 2 is a schematic cross-sectional view of an aluminum substrate with dents arranged in a triangular array after only the anodized porous alumina layer is removed in the first embodiment.
Figure 3:
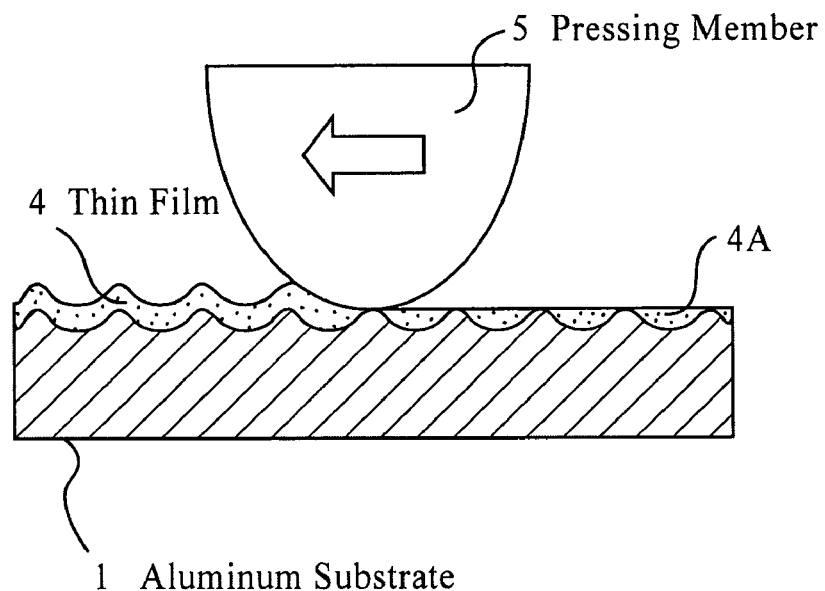
FIG. 3 is a schematic cross-sectional view showing the state of gently pressing a thin film with a plastic spatula in the first embodiment.
Figure 4:
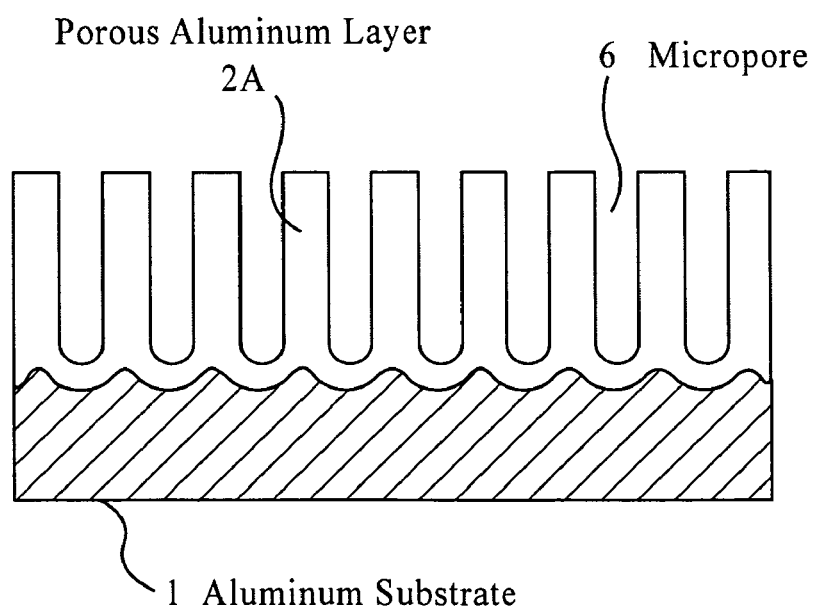
FIG. 4 is a schematic cross-sectional view of an anodized porous alumina layer formed in a second embodiment.
Figure 5:
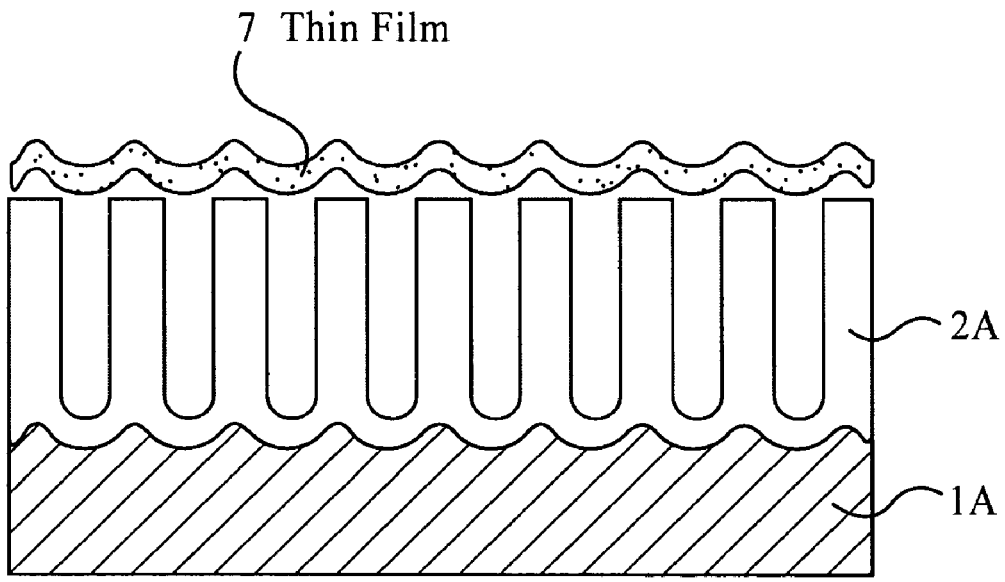
FIG. 5 is a schematic cross-sectional view showing the state in which a thin film is disposed on a surface of the anodized porous alumina layer in the second embodiment.
Figure 6:
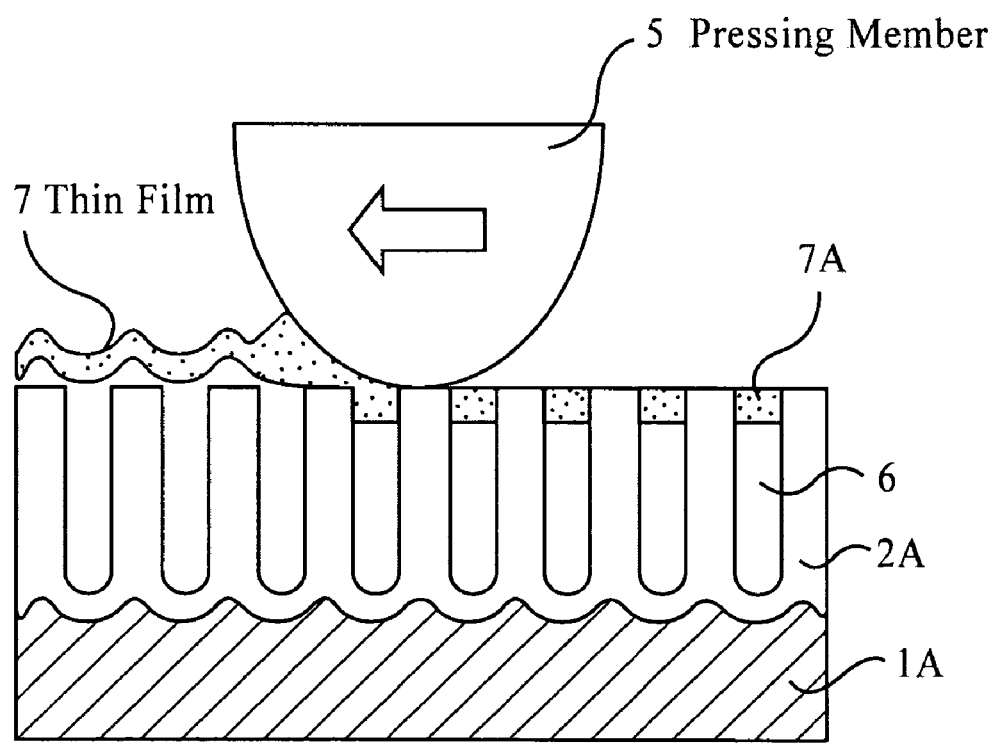
FIG. 6 is a schematic cross-sectional view of the state of gently pressing a thin film with a plastic spatula in the second embodiment.
Figure 7:
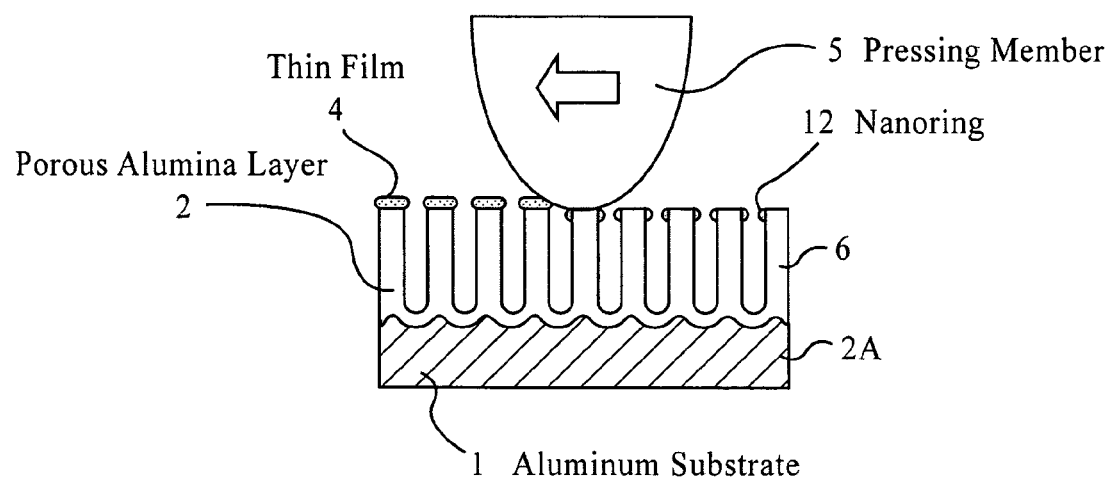
FIG. 7 is a schematic cross-sectional view of the state of gently pressing a thin film with a plastic spatula in the fourth embodiment.
Figure 8:
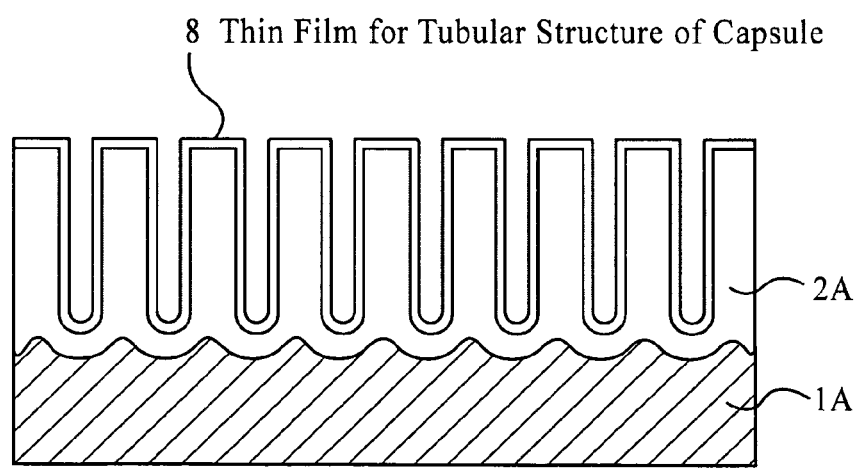
FIG. 8 is a schematic cross-sectional view showing the state of coating micropore wall surfaces in an anodized porous alumina layer with a thin film for capsule tubular structures in a fifth embodiment.
Figure 9:
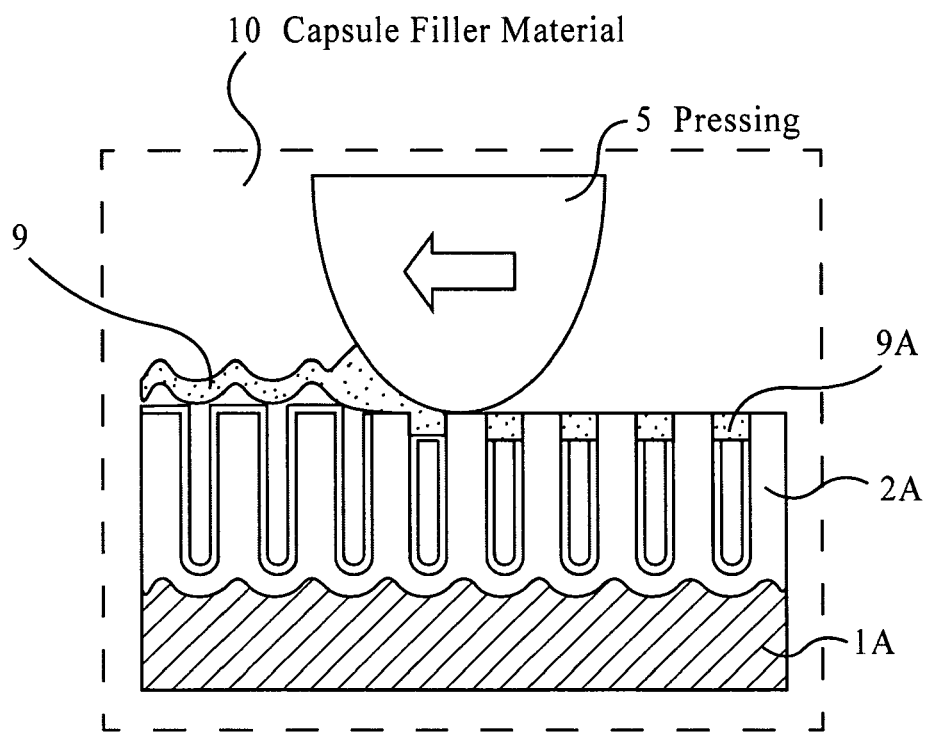
FIG. 9 is a schematic cross-sectional view showing the state of gently pressing a thin-film material for capsule covering with a plastic spatula in the fifth embodiment.
Figure 10:
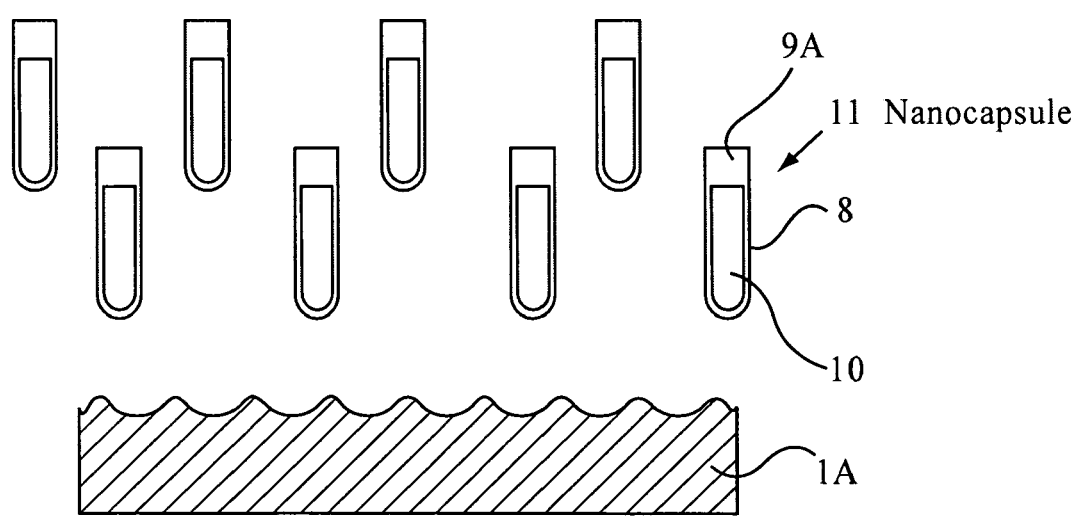
FIG. 10 is a schematic cross-sectional view showing the state of separately recovering nanocapsules by selectively etching the anodized porous alumina layer in the fifth embodiment.
Figure 11:
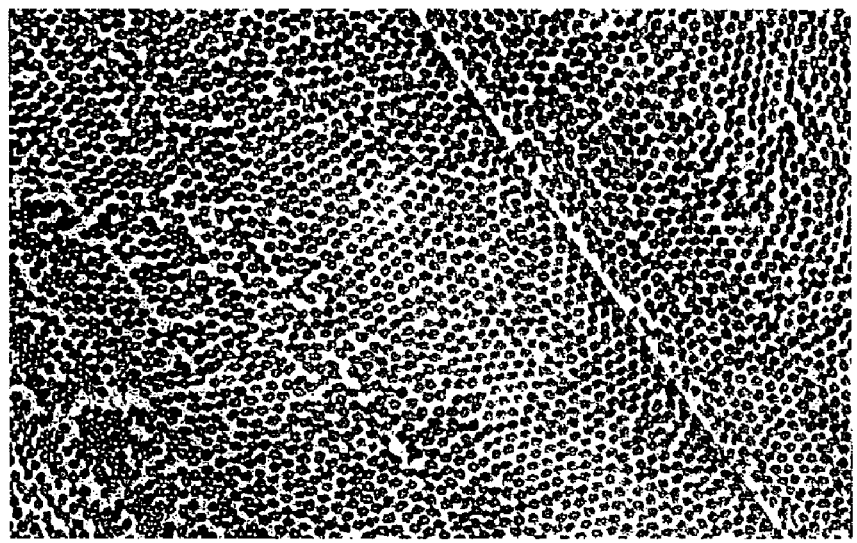
FIG. 11 is a SEM photograph, which substitutes a drawing, showing the state of forming gold microparticles in dents arranged in a triangle array in the first embodiment.
Figure 12:
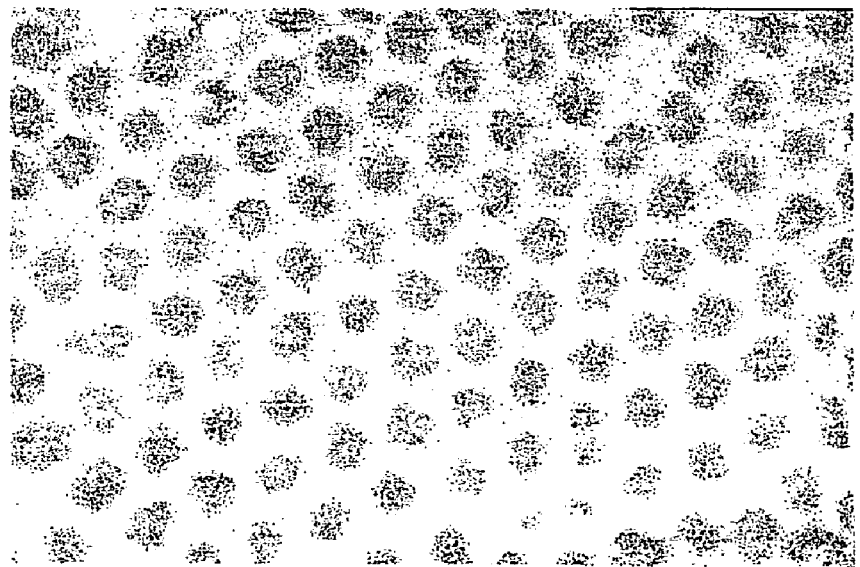
FIG. 12 is a SEM photograph, which substitutes a drawing, showing the state of forming microparticles of a gold thin film filling the vicinity of the surface of the opening of each micropore in the second embodiment.
Figure 13:
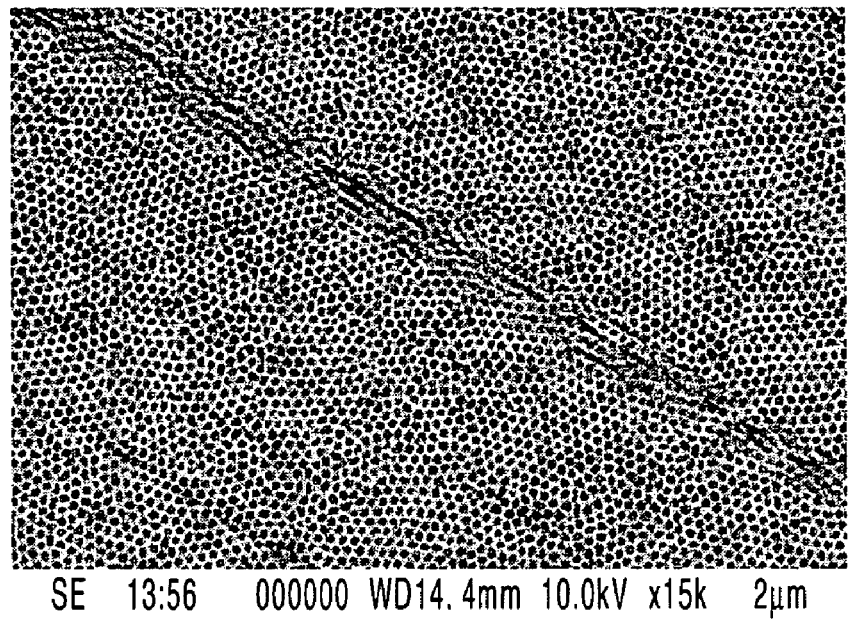
FIG. 13 is a SEM photograph, which substitutes a drawing, showing the state of forming microparticles of a gold thin film filling the vicinity of the surface of the opening of each micropore in the third embodiment.
Figure 14:
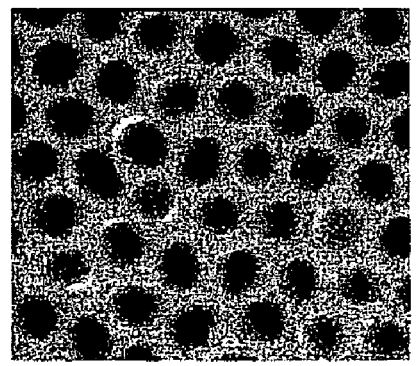
FIG. 14 is a SEM photograph, which substitutes a drawing, showing the state of heat-treated gold microparticles in the third embodiment.
Figures 15A, 15B, 15C:
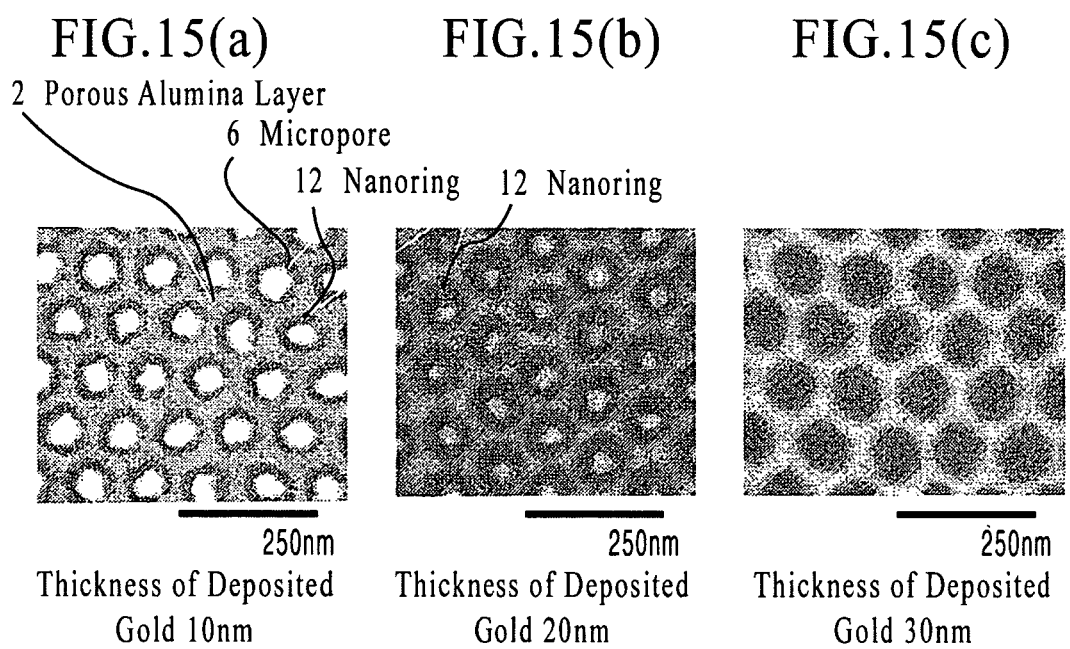
FIG. 15 is a SEM photograph, which substitutes a drawing, showing the state of filling the vicinity of the opening of each micropore with nanoring-shaped microparticles of a gold thin film in the fourth embodiment.
Figure 16:
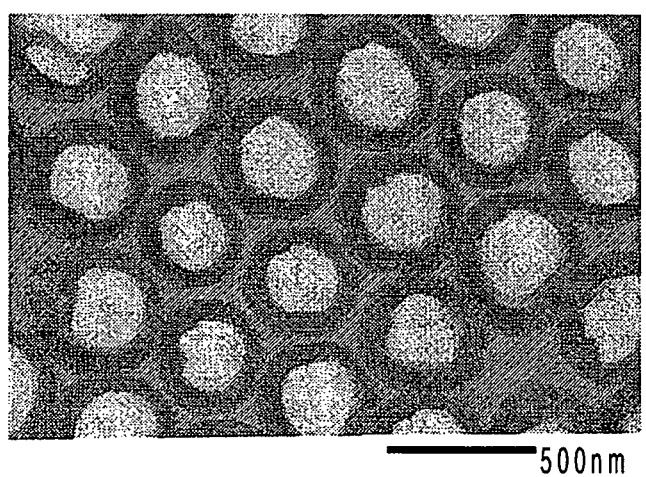
FIG. 16 is a SEM photograph, which substitutes a drawing, showing the state of filling the vicinity of the opening of each micropore with nanoring-shaped microparticles of a gold thin film in the fifth embodiment.

The invention claimed is:

1. A process for producing a nanostructure, comprising:
   disposing a thin-film material on a surface of a nanoporous body, wherein the thin-film material is a solid and selected from the group consisting of a self-supporting film, a thin film formed by vapor deposition or plating, and a thin film made by applying and solidifying a paste material; and
   pressing the thin-film material with a pressing member so that the thin-film material is cut out by surface edges of nanopores of the nanoporous body and a cutout is pressed into the interior of each nanopore,
   wherein a nanostructure constituted from a nanoporous body containing the cutout of the thin-film material in the interior of each nanopore is formed thereby.

2. The process of producing the nanostructure according to claim 1, wherein the thin-film material is disposed on the surface of the nanoporous body in portions other than the openings of the nanopores so that the thin-film material can be cut out and the cutout is pressed into the nanopores in order to form a nanoring shape.

3. The process of producing the nanostructure according to claim 1, wherein the pressing member is a spatula or a ball.

4. A process of producing nanoparticles, comprising: removing the nanoporous body from the nanostructure formed by the process according to any one of claims 1 to 3, wherein the cutout of the thin-film material obtained thereby forms the nanoparticles.

5. The process of producing the nanostructure according to claim 1, wherein the pressing member includes a smooth curved surface.

6. The process of producing the nanostructure according to claim 1, wherein the pressing member is a ball.

7. A process of producing nanocapsules, comprising:
   coating all pore wall surfaces of a nanoporous body with a thin film;
   placing a thin-film material on a surface of the nanoporous body wherein the thin-film material is a solid;
   pressing the thin-film material so that the thin-film material is cut out by surface edges of nanopores of the nanoporous body and the cutout is pressed into the interior of each nanopore to form a nanoporous body in which the cutout of the thin-film material is contained only in the vicinity of an opening of each nanopore; and
   removing the nanoporous body to form a nanocapsule constituted from a tubular structure formed from the thin film that coats the entire wall surface of each nanopore and a cover composed of the cutout of the thin-film material contained in the vicinity of the opening of the nanopore.

* * * * *